United States Patent

Pourrias et al.

Patent Number: 5,132,302
Date of Patent: Jul. 21, 1992

[54] USE OF AROMATIC AMINOALKOXY DERIVATIVES FOR THE TREATMENT OF TROUBLES OF THE CEREBROVASCULAR SYSTEM

[75] Inventors: Bernard M. Pourrias, Bievres; Raphaël Santamaria, Paris; Mona M. Ward, Courbevoie, all of France

[73] Assignee: Delalande S. A., Courbevoie, France

[21] Appl. No.: 515,114

[22] Filed: Apr. 27, 1990

[30] Foreign Application Priority Data

May 5, 1989 [FR] France ............................ 89 05988

[51] Int. Cl.$^5$ ................ A61K 31/55; A61K 31/535; A61K 31/445; A61K 31/40
[52] U.S. Cl. ................ 514/212; 514/317; 514/319; 514/321; 514/422; 514/428; 514/452; 514/651
[58] Field of Search ............ 514/212, 239, 240, 317, 514/319, 321, 422, 428, 239.2, 452, 651

[56] References Cited

U.S. PATENT DOCUMENTS

| | | | |
|---|---|---|---|
| 4,536,500 | 8/1985 | Bourgery et al. | 514/233.8 |
| 4,732,896 | 3/1988 | Bourgery et al. | 514/212 |

*Primary Examiner*—Frederick E. Waddell
*Assistant Examiner*—Diane Gardner
*Attorney, Agent, or Firm*—Zarley, McKee, Thomte, Voorhees & Sease

[57] ABSTRACT

Method of treatment of affections related to a disturbance of the intra and extra cellular movements of calcium at the cerebral level, which comprises administering an aromatic aminoalkoxy derivative of formula (I) or a pharmaceutically acceptable salt thereof:

in which
A represents a chain having any of the following structures:

$$\overset{1}{C}O-\overset{2}{C}H_2-\overset{3}{C}H_2, \quad \overset{1}{C}H-\overset{2}{C}H_2-\overset{3}{C}H_2, \quad \overset{1}{C}H-\overset{2}{\underset{|}{C}}-\overset{3}{C}H_2,$$
$$\quad\quad\quad\quad\quad\quad\quad\quad |\quad\quad\quad\quad\quad\quad | \quad |$$
$$\quad\quad\quad\quad\quad\quad\quad\quad OH\quad\quad\quad\quad\quad OH\;CH_3$$

with middle carbon bearing $CH_3$; and $$\overset{1}{C}O-\overset{2}{\underset{CH_3}{\overset{CH_3}{C}}}-\overset{3}{C}H_2, \quad \overset{1}{C}H_2-\overset{2}{C}H_2-\overset{3}{C}H_2$$

Ar represents a group of structure:

(naphthyl, phenyl with R3, R4 substituents, or benzodioxane structures)

n takes the value 1 or 2 when R is different from H; 'm takes the value 3.

12 Claims, No Drawings

USE OF AROMATIC AMINOALKOXY DERIVATIVES FOR THE TREATMENT OF TROUBLES OF THE CEREBROVASCULAR SYSTEM

The present invention relates to the use of aromatic derivatives comprising an aminoalkoxy chain and salts thereof for the treatment of affections related to disturbances of the intra and extra cellular movements of calcium at the cerebral level and particularly troubles of the cerebrovascular system.

More precisely, said derivatives correspond to the general formula:

$$
\text{Ar}-A-\underset{O-(CH_2)_m-N\underset{R_2}{\overset{R_1}{\diagdown}}}{\underset{}{\bigcirc}}(R)_n \quad (I)
$$

in which

R represents a hydrogen or halogen atom or a methyl, hydroxyl, $C_1$-$C_4$ alkoxy or benzyloxy group;

n takes the value 1 or 2 when R is different from H;

m takes the value 2 or 3;

A represents a chain having any of the following structures:

$$
\overset{1}{CO}-\overset{2}{CH_2}-\overset{3}{CH_2}, \quad \overset{1}{\underset{OH}{CH}}-\overset{2}{CH_2}-\overset{3}{CH_2},
$$

$$
\overset{1}{CH}-\overset{2}{\underset{CH_3}{\overset{CH_3}{C}}}-\overset{3}{CH_2}, \quad \overset{1}{CO}-\overset{2}{\underset{CH_3}{\overset{CH_3}{C}}}-\overset{3}{CH_2}, \quad \overset{1}{CH_2}-\overset{2}{CH_2}-\overset{3}{CH_2}.
$$

the aromatic group Ar being bonded to position 1 of this chain the pair ($R_1$, $R_2$) takes the value (H, $C_1$-$C_4$ alkyl), (H, $C_5$-$C_6$ cycloalkyl) or (H, cycloalkylalkyl comprising 4 to 8 carbon atoms), except in the case where $$
A = CO-\underset{CH_3}{\overset{CH_3}{\underset{|}{C}}}-CH_2 \quad \text{or} \quad CH-\underset{OH}{\overset{CH_3}{\underset{|}{C}}}-CH_2.
$$

or else the value ($C_1$-$C_4$ alkyl, $C_1$-$C_4$ alkyl). $R_1$ and $R_2$ being also able to form jointly with the nitrogen atom with which they are bonded, a radical chosen from the following: pyrrolidino, piperidino, hexamethyleneimino, morpholino; and Ar represents:

either a benzenic-group of structure:

$$
\underset{(R_4)_q}{\overset{(R_3)_p}{\bigcirc}}
$$

in which $R_3$ represents a halogen atom or a nitro or methyl group, $R_4$=alkoxy with 1 to 4 carbon atoms, $p=0$, 1 or 2, $q=0$, 1, 2, 3 or 4, $p+q \leq 4$, with the restrictions that when $$
A = CO-CH_2-CH_2 \quad \text{or} \quad \underset{OH}{\overset{}{CH}}-CH_2-CH_2
$$

p and q cannot take simultaneously the value 0, or a naphthalenic or benzodioxannic group respectively of structure:

$$
\underset{R_4}{\overset{R_4}{\bigcirc\bigcirc}}, \quad \underset{R_4}{\overset{R_4}{\bigcirc\text{O}\bigcirc}}
$$

where $R_4$ has the same meanings as above.

As for the salts of the derivatives of formula (I), they are formed by the pharmaceutically acceptable mineral acid addition salts such as salts with hydrochloric acid and pharmaceutically acceptable organic acid addition salts such as salts with oxalic acid.

As examples of derivatives of formula (I) and their pharmaceutically acceptable salts, those shown in Table 1 hereafter may be mentioned.

TABLE I $$\begin{array}{c} (R)_n \\ \diagdown \\ \text{Ar—O—(CH}_2)_m\text{—N} \diagup R_1 \\ \diagdown R_2 \end{array} \quad (I)$$

| Code No. | —A— | (R)$_n$ | m | $\begin{array}{c}R_1\\ \diagdown\\ —N\\ \diagup\\ R_2\end{array}$ | Ar—O— | Empirical formula | Molecular weight | Melting point (°C.) | Form | Elementary analysis or NMR Spectrum % | C | H | N |
|---|---|---|---|---|---|---|---|---|---|---|---|---|---|
| 1 | —CO—CH$_2$—CH$_2$— | 4-OH | 2 | piperidine | 2,4,5-tri-OCH$_3$ phenyl | C$_{24}$H$_{31}$NO$_5$ | 413.49 | 88 | Base | NMR(CDCl$_3$) δppm=6.82, m and 6.10, s(6 aromatic H); 4.1, t(OC$\underline{H}_2$); 3.72 and 3.8, s(2C$\underline{H}_3$O); 2.4 to 3, m(10H:COCH$_2$CH$_2$ and CH$_2$—N$\diagdown \begin{array}{c}\underline{CH}_2\\ \underline{CH}_2\end{array}$); 1.5, m(CH$_2$—CH$_2$—CH$_2$) | | | |
| 2 | —CO—CH$_2$—CH$_2$— | " | " | " | 2,3,4-tri-OCH$_3$ phenyl | C$_{24}$H$_{32}$ClNO$_5$ | 449.96 | 181 | HCl | Cal. Obt. | 64.06 63.98 | 7.17 7.09 | 3.11 3.08 |
| 3 | —CH—CH$_2$—CH$_2$— $\diagup$ OH | H | " | " | " | C$_{24}$H$_{33}$NO$_4$ | 399.51 | 79 | Base | Cal. Obt. | 72.15 72.04 | 8.33 8.51 | 3.51 3.45 |
| 4 | " | 4-F | " | " | " | C$_{24}$H$_{32}$FNO$_4$ | 417.50 | Oil | " | Cal. Obt. | 69.04 68.49 | 7.73 7.56 | 3.36 3.15 |
| 5 | —CH—CH$_2$—CH$_2$— $\diagup$ OH | 4-Cl | 2 | piperidine | 2,3,4-tri-OCH$_3$ phenyl | C$_{24}$H$_{32}$ClNO$_4$ | 433.96 | Oil | Base | Cal. Obt. | 66.42 65.80 | 7.43 7.95 | 3.23 3.34 |
| 6 | " | 4-CH$_3$ | " | " | " | C$_{25}$H$_{35}$NO$_4$ | 413.54 | " | " | Cal. Obt. | 72.61 72.31 | 8.53 8.58 | 3.39 3.27 |
| 7 | " | 4-CH$_3$O | " | " | " | C$_{25}$H$_{35}$NO$_5$ | 429.54 | " | " | Cal. Obt. | 69.90 69.25 | 8.21 8.33 | 3.26 3.14 |

TABLE I-continued

| # | R | Pos | n | Amine | Ar | Formula | MW | mp | Salt | | C | H | N |
|---|---|---|---|---|---|---|---|---|---|---|---|---|---|
| 8 | " | 2-CH | " | " | " | C₂₄H₃₄ClNO₅ + 4% H₂O | 470.81 | 88 | HCl + 4% H₂O | Cal.<br>Obt. | 61.22<br>61.50 | 7.73<br>7.93 | 2.98<br>2.97 |
| 9 | —CH—CH₂—CH₂—<br>  \|<br>  OH | 3-OH | 2 | piperidine (N-) | 2-CH₃, 3-OCH₃, 4-OCH₃ (trimethoxy/methyl phenyl) | C₂₄H₃₃NO₅ | 415.52 | 128 | Base | Cal.<br>Obt. | 69.31<br>69.25 | 8.01<br>8.02 | 3.37<br>3.19 |
| 10 | " | 4-OH | " | " | " | C₂₄H₃₃NO₅ | 415.52 | 142 | " | Cal.<br>Obt. | 69.31<br>69.29 | 8.01<br>8.10 | 3.37<br>3.21 |
| 11 | " | " | 3 | " | " | C₂₅H₃₅NO₅ | 429.54 | 118 | " | Cal.<br>Obt. | 69.90<br>69.95 | 8.21<br>8.35 | 3.26<br>3.30 |
| 12 | " | " | 2 | NEt₂ | " | C₂₃H₃₃NO₅ | 403.50 | 90 | " | Cal.<br>Obt. | 68.46<br>68.28 | 8.24<br>8.39 | 3.47<br>3.46 |
| 13 | —CH—CH₂—CH₂—<br>  \|<br>  OH | 4-OH | 2 | pyrrolidine (N-) | 2-CH₃, 3-OCH₃, 4-OCH₃ | C₂₃H₃₁NO₅ | 401.49 | 159 | Base | Cal.<br>Obt. | 68.80<br>68.14 | 7.78<br>7.84 | 3.49<br>3.52 |
| 14 | " | " | " | piperidine (N-) | 2-OCH₃, 3-CH₃, 4-OCH₃, 5-OCH₃, 6-OCH₃ | C₂₅H₃₅NO₆ + 3/4 HOOC—COOH | 513.06 | 175 | 3/4 oxalate | Cal.<br>Obt. | 62.03<br>61.89 | 7.17<br>7.32 | 2.73<br>2.73 |
| 15 | " | " | " | " | 2-OCH₃, 3-CH₃, 4-OCH₃, 5-OCH₃, 6-OCH₃ | C₂₅H₃₅NO₆ | 445.54 | 117 | Base | Cal.<br>Obt. | 67.39<br>67.16 | 7.92<br>8.08 | 3.14<br>2.89 |

TABLE I-continued

| | | Ar | | Formula | MW | mp | | Analysis | C | H | N |
|---|---|---|---|---|---|---|---|---|---|---|---|
| 16 | " | " | 2-OCH₃, 3-OCH₃ (ortho-dimethoxy) | C₂₄H₁₂NO₆ + 1.2% H₂O | 435.56 | 148 | 0.5 oxalate + 1.2% H₂O | Cal. Obt. | 66.17 66.32 | 8.00 7.62 | 3.22 3.17 |
| 17 | −CH−CH₂−CH₂− / OH | 4-OH | 2,3,4-triOCH₃ | C₂₃H₃₁NO₆ | 417.49 | 107 | Base | Cal. Obt. | 66.17 65.88 | 7.48 7.70 | 3.36 3.47 |
| 18 | " | morpholine | " | C₂₁H₂₉NO₅ + 1.1% H₂O | 379.70 | 105 | Base + 1.1% H₂O | Cal. Obt. | 66.43 66.03 | 7.83 7.98 | 3.69 3.86 |
| 19 | " | N(CH₃)₂ | CH₃O-/CH₃O-/OCH₃ (trimethoxy) | C₂₄H₃₅NO₆ | 433.53 | 112 | Base | Cal. Obt. | 66.49 66.40 | 8.14 8.48 | 3.23 2.93 |
| 20 | " | N(Et)₂ | 2-OCH₃, OCH₃ | C₂₅H₃₃NO₈ + 1.7% H₂O | 483.75 | 103 | Oxalate 1.7% H₂O | Cal. Obt. | 62.07 62.24 | 7.07 7.14 | 2.90 3.04 |
| 21 | −CH−CH₂−CH₂− / OH | 4-O-CH₂-φ | piperidine | 2,5-diOCH₃, OCH₃ | C₃₁H₃₉NO₅ | 505.63 | Oil | Oxalate 1.7% H₂O | | | |

NMR(CDCl₃) δppm = 6.8 to 7.5, m(9 aromatic H); 6.25, s(2 aromatic H in 3 and 5); 5.05, s(OCH₂-φ); 5.1, m(CH−O); 4.1, m(OH and OCH₂); 3.8, s(2CH₃O); 2 to 2.8, m(10H: −CH₂−CH₂− and CH₂−N−CH₂ ); 1.4 to 1.8, m(−N ).

TABLE I-continued

| Code No. | Ar—O— | —A— | $(R)_n$ | m | $\begin{array}{c}R_1\\ \diagdown\\ N\\ \diagup\\ R_2\end{array}$ | Form | Empirical formula | Molecular weight | Melting point (°C.) | ELEMENTARY ANALYSIS % or NMR spectrum | | | |
|---|---|---|---|---|---|---|---|---|---|---|---|---|---|
| | | | | | | | | | | | C | H | N |
| 22 | [Ar = 2-methyl-3,5-dimethoxyphenyl with OH, —CH—CH$_2$—CH$_2$—] | 3,4-di-$\phi$-O-CH$_2$— | | | [piperidine] | Base | C$_{38}$H$_{45}$NO$_6$ | 611.75 | | | | | |
| | | | | | | | | | | Cal. Obt. | | 7.51 7.42 | 2.85 2.67 |
| | | | | | | | | | | | 58.63 58.66 | | |
| 23 | " | 3,4-diCH | " | | " | " | C$_{24}$H$_{34}$ClNO$_6$ + 4.8% H$_2$O | 491.57 | 140 | HCl + 4.8% H$_2$O | | | |

NMR(CDCl$_3$) $\delta$ppm=7.2 to 7.6, m(10 benzylic H); 6.6 to 6.9, m(aromatic H); 5.1. s(2OCH$_2\phi$); 5 to 5.3., m(OH and CH—O); 4.4 and 3.4, m(OCH$_2$); 3.7 and 3.78, s(2CH$_3$O); 2.2 to 2.6, m and 1.4. to 1.8, m(CH$_2$CH$_2$ and CH$_2$—N $$\underset{\text{Ar}}{\text{Ar}-\text{O}-\text{A}-\overset{(R)_n}{\underset{|}{\bigcirc}}-\text{O}-(CH_2)_m-\overset{R_1}{\underset{R_2}{N}}} \quad (I)$$

| Code No. | Ar—O— | —A— | $(R)_n$ | m | $\begin{array}{c}R_1\\N\\R_2\end{array}$ | Form | Empirical formula | Molecular weight | Melting point (°C.) | ELEMENTARY ANALYSIS % | | | |
|---|---|---|---|---|---|---|---|---|---|---|---|---|
| | | | | | | | | | | | C | H | N |
| 60 | [2-methyl-3,5-dimethoxy-4-OCH$_3$ phenyl] | —(CH$_2$)$_3$— | OH | 2 | [piperidine] | Base | C$_{24}$H$_{33}$NO$_4$ | 399.51 | 136 | Cal. Obt. | 72.15 71.94 | 8.33 8.44 | 3.51 3.38 |
| 61 | [chloro-dimethoxy-methyl phenyl] | —CO—CH$_2$—CH$_2$— | " | " | " | " | C$_{24}$H$_{30}$ClNO$_5$ | 447.94 | 120 | Cal. Obt. | 64.35 64.22 | 6.75 6.96 | 3.13 2.94 |
| 62 | [2-methyl-3,5-dimethoxyphenyl] | —CH—CH$_2$—CH$_2$—<br>$\phantom{xxx}$—CH | " | " | [2,6-dimethylpiperidine] | " | C$_{25}$H$_{37}$NO$_5$ | 431.55 | 75 | Cal. Obt. | 69.57 69.19 | 8.64 8.82 | 3.25 3.51 |

TABLE I-continued

| # | Aryl | R | n | Amine | Form | Formula | MW | mp | | Anal % C | H | N |
|---|---|---|---|---|---|---|---|---|---|---|---|---|
| 63 | 2,3,4-tri-OCH₃ phenyl | -CH(OH)-CH₂-CH₂- | 2 | cyclopentyl-NH- | Oxalate | C₂₆H₃₅NO₉ | 505.55 | 197 | Cal.<br>Obt. | 61.77<br>61.52 | 6.98<br>7.36 | 2.77<br>2.88 |
| 64 | 3-OCH₃, 4-OCH₃, 5-CH₃ phenyl | " | OH 2 | piperidino | Base | C₂₄H₃₃NO₅ | 415.51 | 128 | Cal.<br>Obt. | 69.37<br>68.86 | 8.01<br>8.00 | 3.37<br>3.36 |
| 65 | 3-OEt, 4-OCH₃, 5-OEt phenyl | " | " | N(Et)₂ | " | C₂₅H₃₇NO₅ | 431.55 | 80 | Cal.<br>Obt. | 69.57<br>69.07 | 8.64<br>8.77 | 3.25<br>3.44 |
| 66 | benzodioxane-OCH₃,OCH₃ | " | " | piperidino | Base | C₂₆H₃₅NO₇ | 473.55 | 158 | Cal.<br>Obt. | 65.94<br>65.63 | 7.45<br>7.39 | 2.96<br>2.82 |
| 67 | tetra-OCH₃ phenyl | -CH(OH)-CH₂-CH₂- | OH 2 | piperidino | Chlorhydrate | C₂₆H₃₈ClNO₇ | 512.03 | 105 | Cal.<br>Obt. | 60.98<br>60.65 | 7.48<br>7.79 | 2.74<br>2.91 |
| 68 | dimethoxy naphthyl | -CH(OH)-CH₂-CH₂- | CH 2 | piperidino | Base + 0.8% H₂O | C₂₈H₃₅NO₅ + 0.8% H₂O | 469.32 | 180 | Cal.<br>Obt. | 71.65<br>71.47 | 7.61<br>7.84 | 2.99<br>2.91 |

(Oxalate)

TABLE I-continued

| # | Aryl | R | R' | Amine | Form | Formula | MW | mp (°C) | | C | H | N |
|---|---|---|---|---|---|---|---|---|---|---|---|---|
| 69 | 3-OCH₃, 4-OCH₃, 6-Cl, (2-CH₃) phenyl | " | " | " | Base<br>Oxalate | C₂₄H₃₂ClNO₅<br>C₂₆H₃₄ClNO₉ | 449.96<br>539.99 | 116<br>131 | Cal.<br>Obt. | 57.83<br>57.67 | 6.35<br>6.47 | 2.59<br>2.88 |
| 70 | " | " | " | Et₂N– (diethylamino) | Base | C₂₃H₃₂ClNO₅ | 437.95 | 124 | Cal.<br>Obt. | 63.07<br>62.80 | 7.37<br>7.46 | 3.20<br>3.23 |
| 71 | " | " | " | (iPr)₂N– (diisopropylamino) | | C₂₅H₃₆ClNO₅ | 466.00 | 102 | Cal.<br>Obt. | 64.43<br>64.51 | 7.79<br>8.05 | 3.01<br>2.98 |
| 72 | 3-OCH₃, 4-OCH₃, 6-F, (2-CH₃) phenyl | –CH(OH)–CH₂–CH₂– | 2 | piperidino | Base | C₂₄H₃₂FNO₅ | 433.50 | 122 | Cal.<br>Obt. | 66.49<br>66.43 | 7.44<br>7.53 | 3.23<br>3.01 |
| 73 | 3-OCH₃, 4-OCH₃, 6-Cl, (2-CH₃) phenyl | " | " | " | " | C₂₄H₃₂ClNO₅ | 449.96 | 132 | Cal.<br>Obt. | 64.06<br>63.95 | 7.17<br>6.89 | 3.11<br>2.83 |
| 74 | 3-OCH₃, 4-OCH₃, 6-NO₂, (2-CH₃) phenyl | " | " | " | " | C₂₄H₃₂N₂O₇ | 460.51 | 162 | Cal.<br>Obt. | 62.59<br>62.84 | 7.00<br>7.40 | 6.08<br>5.99 |

TABLE I-continued

| # | Aryl | R | R' | n | Amine | Form | Formula | MW | mp (°C) | Analysis | C | H | N |
|---|---|---|---|---|---|---|---|---|---|---|---|---|---|
| 75 | 2,6-Cl$_2$-3-OCH$_3$-phenyl | -CH(OH)-CH$_2$- | OH | 2 | piperidine | Base | C$_{22}$H$_{27}$Cl$_2$NO$_3$ | 424.36 | 147 | Cal. / Obt. | 62.26 / 62.41 | 6.41 / 6.60 | 3.30 / 3.25 |
| 76 | 4-Cl-2-OCH$_3$-phenyl | -CH(OH)-CH$_2$- | OH | 2 | piperidine | Base | C$_{22}$H$_{28}$ClNO$_3$ | 389.91 | 153 | Cal. / Obt. | 67.76 / 67.74 | 7.24 / 7.41 | 3.59 / 3.58 |
| 77 | 2-OCH$_3$-phenyl | -C(CH$_3$)$_2$-CH$_2$- (with OH) | " | " | " | HCl | C$_{24}$H$_{34}$ClNO$_3$ | 419.98 | 210 | Cal. / Obt. | 68.63 / 68.72 | 8.16 / 8.10 | 3.34 / 3.32 |
| 78 | 3,5-OCH$_3$-4-Cl-phenyl | -CH(OH)-CH$_2$- | H | " | " | base | C$_{24}$H$_{32}$ClNO$_4$ | 433.96 | 89 | Cal. / Obt. | 66.42 / 66.50 | 7.43 / 7.51 | 3.23 / 3.29 |
| 79 | " | -(CH$_2$)$_3$- | CH | " | " | Oxalate | C$_{26}$H$_{34}$ClNO$_8$ | 523.99 | 164 | Cal. / Obt. | 59.59 / 59.73 | 6.54 / 6.43 | 2.67 / 2.96 |
| 80 | 2-OCH$_3$-phenyl | -CO-C(CH$_2$)$_2$- | CCH$_2$φ | 2 | piperidine | Base | C$_{31}$H$_{37}$NO$_3$ | 471.61 | <50 | NMR:(CDCl$_3$) δ ppm=6.6 to 7.4, m(13 aromatic H); 5.0, s(CH$_2$-φ); 4.0, t and 2.6, t(O-CH$_2$-CH$_2$); 2.85, s(CH$_2$); 2.4, m(4 piperidinic H); 1.4, m(6 piperidinic H); 1.15, s(2CH$_3$) | | | |
| 81 | " | " | CH | " | " | " | C$_{24}$H$_{31}$NO$_3$ | 381.49 | Oil | NMR(CDCl$_3$) δ ppm = 7.4, m(OH); 6.6 to 7.2, m(8 aromatic H); 4.05 and 2.6, (O-CH$_2$-CH$_2$); 2.8, s(CH$_2$); 1.15, s(2CH$_3$); 2.5 and 1.55, m(10 piperidinic H). | | | |
| 82 | 3,5-OCH$_3$-4-Cl-phenyl | -CH(OH)-CH$_2$- | OCH$_2$φ | " | " | " | C$_{31}$H$_{38}$ClNO$_5$ | 541.08 | " | NMR(CDCl$_3$) δppm = 7.4, s(5 benzylic H): 6.5 to 7.2, m(5 aromatic H); 5, s(OCH$_2$); 5.05, m(OH); 4.2, 2.7, m(C$\underset{OH}{\overset{H}{|}}$); 3.65 and 3.75, s(CH$_3$O); 3.7 and 2.7, m(OCH$_2$-CH$_2$); 2.4 and 1.5, m(10 piperidinic H) | | | |

TABLE I-continued

| # | Aryl group | R | R' | Amine (Base) | Formula | MW | mp/form | NMR / Analysis |
|---|---|---|---|---|---|---|---|---|
| 83 | OCH$_3$, OCH$_3$, F-substituted aryl with OCH$_3$ | —CH(OH)—CH$_2$— | " | " | C$_{31}$H$_{38}$FNO$_5$ | 523.62 | " | NMR(CDCl$_3$) δ ppm=7.4, s(5 benzylic H); 6.8, d and 7.10, d(4 aromatic H); 6.4, d(J H—F)(1 aromatic H); 5.05, m(C$\underline{H}$—O); 4.5, 4.0 and 2.8, s(C$\underline{H_2}$); 5, s(CH$_2$); m(OCH$_2$CH$_2$—); 3.65 and 3.8, s(CH$_3$O); 2.4 and 1.6, m(10 piperidinic H) |
| 84 | OCH$_3$, OEt, OEt aryl | —CH(OH)—CH$_2$— | OCH$_2$φ | Et$_2$N (Base) | C$_{32}$H$_{43}$NO$_5$ | 521.67 | Oil | NMR(CDCl$_3$) δ ppm=7.35, s(5 benzylic H); 6.4 to 7.4, m(6 aromatic H); 5.35, m(OH); 5, s(CH$_2$); 4.45, m(CH—O); 3.6 to 4.10, m(3-OCH$_2$); 2.4 to 2.8, m)(CH$_2$—CH$_2$— and N(CH$_2$)$_3$:10 protons); 0.9 to 1.4, m(12H; 4CH$_3$) |
| 85 | OCH$_3$, OCH$_3$ aryl | " | " | cyclopentyl-NH | C$_{31}$H$_{39}$NO$_5$ | 505.63 | " | NMR(CDCl$_3$), δ ppm=7.35, s(5 benzylic H); 6.5 to 7.4, m(6 aromatic H); 5, s(CH$_2$) and 5.05, m(CH—O); 3.65 and 3.75, s(OCH$_3$); 4.10, m and 1.4 to 3.4, m(18 protons) |
| 86 | OCH$_3$, OCH$_3$, OCH$_3$, OCH$_3$ naphthyl | " | OCH$_2$φ | piperidine | C$_{35}$H$_{41}$NO$_5$ | 555.69 | " | NMR:(CDCl$_3$) δppm=8, s and 6.7 to 7.4(13 aromatic H); 5, s(CH$_2$); 3.85, s(2OCH$_3$); 4.5, m and 1.4 to 2.8, m(19 protons) |
| 87 | OCH$_3$, Cl aryl | —CO—CH$_2$— | CH | " | C$_{22}$H$_{26}$ClNO$_3$ | 387.89 | " | |
| 88 | OCH$_3$, Cl, Cl, OCH$_3$ aryl | —CH(OH)—CH$_2$— | OH | piperidine (Base) | C$_{24}$H$_{31}$Cl$_2$NO$_5$ | 484.41 | 146 | NMR(CDCl$_3$) δppm=9.3, m(CH); 6.6 to 7.6, m(7 aromatic H); 4.2 and 2.6, t((OCH$_2$—CH$_2$—); 3.25 and 2.7; t((CO—CH$_2$—CH$_2$); 2.4 and 1.5, m(10 piperidinic H)<br>Cal. 59.50  6.45  2.89<br>Obt. 58.80  6.56  2.59 |

TABLE I-continued

| # | Ar | R | CH | n | Amine | Form | Formula | MW | m.p. °C | | Analysis C H N |
|---|---|---|---|---|---|---|---|---|---|---|---|
| 89 | OCH₃ / OCH₃ / CH₃ (ring) | —OH / —CH(CH₃)—CH₂— | CH | 2 | piperidine | Base | C₂₄H₃₃NO₄ | 399.51 | Oil | | NMR(CDCl₃) δppm=between 6.4 and 7.2, m(6 aromatic H); 5.7, s(OH and phenolic OH); 5.1, t(H in α of OH); 3.98, t(—OCH₂); 3.75, s(OCH₃); 2.2, s(CH₃); 2.4, m(CH₂—CH₂ and 3CH₂ in α of nitrogen); 1.5, m(6 piperidinic H). |
| 90 | OCH₃ / OCH₃ / Cl (ring) | —OH / —CH / CH₂— (gem-dimethyl) | " | " | " | " | C₂₆H₃₆ClNO₅ | 478.01 | 162 | Cal. Obt. | 65.32 7.59 2.93 / 64.77 5.62 2.68 |
| 91 | OCH₃ / OCH₃ / Cl (ring) | —CO— / CH₂— (gem-dimethyl) | " | " | " | " | C₂₆H₃₄ClNO₅ | 475.99 | 140 | Cal. Obt. | 65.60 7.20 2.94 / 65.08 7.24 2.67 |
| 92 | OCH₃ / Cl (ring) | OH / —CH—CH₂— / CH₂— | OH | 2 | piperidine | Base | C₂₃H₃₀ClNO₄ | 419.93 | 126 | Cal. Obt. | 65.78 7.20 3.34 / 65.77 7.33 3.33 |

The derivatives of formula (I) and their pharmaceutically acceptable salts are described in the American patents 4 536 500 and 4 732 896 and in the Belgian patent 895 464, which patents contain all the useful information concerning the methods of preparing said derivatives and salts, their physico-chemical properties and their toxicity.

These derivatives and salts are known from these patents, as having a calcium antagonistic activity revealed by the test of depolarizing the isolated coronary arteries of a dog, from which test it was concluded that said derivatives and salts found their usefulness in the treatment of troubles of the cardiovascular system.

It has now been unexpectedly discovered that the derivatives of formula (I) and their salts further have a calcium antagonistic activity at the cerebral level. Such activity was revealed by the test of contractions of the isolated balisar artery of a rabbit in a hypopotassic medium as described by K. Towart, S. Kazda in Nimodipine Pharmacological Properties, published by P. E. Betz, K. Deck and F. Hoffmeister (1984), publisher E. K. Schattauer Verlag.

The protocol of this test is the following. The rabbit is anaesthetized with pentobarbital at a dose of 30 mg/kg then sacrificed by exsanguination and decapitated at the level of the third cervical vertebra. The balisar artery is removed (1.5 cm) between the vertebral arteries and the polygon of Willis. The balisar artery is then cut in a spiral at an angle of 45°. It is fixed by means of a curved needle between an L shaped glass carrier and a displacement sensor (Grass, type FT03). A mechanical tension of 500 mg is applied to the vessel before letting it reach its balance state.

For a period of an hour, the vessel is rinsed every twenty minutes until a stable level is obtained.

The tonic contraction consecutive to depolarization caused by KCl is dependent on the calcic movements for it is abolished by the suppression of calcium in the survival medium.

The $IC_{50}$ (in M/l) concentrations are measured which reduce by 50% the amplitude of the contraction induced by KCl at 35 mmoles.

The results obtained with some derivatives of formula (I) in the above test are given by way of example in Table II below.

TABLE II

| Code no. of derivative tested | $IC_{50}$ (M/l) |
| --- | --- |
| 3 | $4 \times 10^{-7}$ |
| 10 | $2.6 \times 10^{-8}$ |
| 69 | $2.3 \times 10^{-9}$ |
| 70 | $7.2 \times 10^{-9}$ |
| 71 | $9.8 \times 10^{-9}$ |
| 72 | $3 \times 10^{-9}$ |
| 74 | $1.4 \times 10^{-9}$ |

Consequently a first object of the invention resides in the use of the derivatives of formula (I) and their pharmaceutically acceptable salts in human or animal therapeutics for the treatment of affections related to a disturbance of the intra and extra cellular movements of calcium at the cerebral level and particularly troubles of the cerebrovascular system, such as cerebral haemorrhages, cerebral infarction and migraine.

An other object of the present invention is a method of treatment of the above-mentioned affections, which method comprises administering an effective amount of a derivative of formula (I) or a pharmaceutically acceptable salt thereof.

The administration of said derivative or salt may be by way of oral, parenteral or rectal administration.

Still another object of the present invention resides in the use of the derivatives of formula (I) and their pharmaceutically acceptable salts for the preparation of medicaments for the treatment of the above mentioned affections and particularly pharmaceutical compositions which comprise at least one of these derivatives and salts in association with a physiologically acceptable carrier or excipient appropriate for said compounds.

Such compositions may for example be formulated with a view to the administration orally, parenterally or rectally.

For oral administration, said compositions may be in the form of tablets, pills, or capsules prepared by the usual techniques using known carriers and excipients such as diluents (e.g. polyethylene glycol, lactose, dextrose), binders (e.g. starch, arabic gum, gelatin, methycellulose, carboxymethycellulose, polyvinyl pyrrolidone), fillers, lubricants (e.g. magnesium or calcium stearate, stearic acid, talc, silica) and disintegration agents (e.g. starch, alginic acid, alginate). These compositions, for oral administration, may also take the form of solutions, syrups or suspensions; the syrups may contain, by way of carrier, for example saccharose with possibly glycerine and/or mannitol and/or sorbitol; the suspensions may contain, as carrier, for example a natural gum, agar, sodium alginate, pectin or methylcellulose; as for the solutions, they may be aqueous solutions.

For parenteral administration, the compositions according to the invention may take the form of injectable solutions, suspensions, or emulsions, comprising a parenterally acceptable liquid, oily or aqueous vehicle, (for example sterile water, olive oil, ethyl oleate, propylene glycol in the case of the forms for intramuscular injection and sterile water or sterile isotonic saline aqueous solutions in the case of the forms for intravenous injection).

Finally, for rectal administration, the compositions of the invention may take the form of suppositories comprising the usual bases for suppositories (e.g. cocoa butter, polyethylene glycol).

The dose at which the active ingredients, namely the derivatives of formula (I) and their salts, may be administered to man or any hot-blooded animal, depends on the type of administration, the body weight and the pathological state of the patient and the therapeutic power of the derivatives and salts used. Generally, orally, the doses may reach 500 mg of active ingredient per day (taken in one or more times); parenterally, the doses may reach 100 mg of active ingredient per day (taken in one or more daily injections) and rectally, the doses may reach 300 mg of active ingredient per day (one or more suppositories).

For illustrating the present invention, some examples of pharmaceutical compositions are given hereafter formed from the compounds of formula (I):

EXAMPLE 1 preparation of tablets.

The following constituents are intimately mixed:
100 mg of the compound of code no. 3
20 mg of lactose
4 mg of sodic carboxymethyl starch
4 mg of polyvinyl pyrrolidone
2 mg of magnesium stearate.

With this mixture divisible tablets are produced (having two dividing grooves) each weighing 130 mg.

EXAMPLE 2 preparation of tablets with the following constituents:

10 mg of the compound of code no. 10
100 mg of lactose
8 mg of maize starch
8 mg of polyvinyl pyrrolidone
4 mg of magnesium stearate.

Tablets are manufactured as in the preceding example having a final weight of 130 mg.

EXAMPLE 3 preparation of a solution for oral administration.

The preparation of such a solution containing 10 mg of active ingredient for 5 ml of solution is achieved by dissolving:

0.2 g of the compound of code no. 69
0.1 g of methyl parahydroxybenzoate
0.1 g of propyl parahydroxybenzoate
q.s.p. 100 ml of purified water.

EXAMPLE 4 preparation of a syrup.

The preparation of a syrup containing 100 g of active ingredient for 5 ml of syrup is achieved by mixing:

2 g of the compound of code no. 13
40 g of saccharose
10 g of glycerine
sweetening and flavouring
q.s.p. 100 ml of purified water.

We claim:

1. A method of treatment of affections of the cerebrovascular system in human or animal, which comprises administering to a human or animal in need in such treatment a small but cerebrally effective amount of an aromatic aminoalkoxy derivative of formula (I) or a pharmaceutically acceptable salt thereof to achieve a calcium antagonistic activity only at the cerebrovascular level, said amount is at a dose lower than the required level to achieve cardiovascular calcium antagonistic activity, preferably at a level of IC50 of about $10^{-9}$ moles $$\text{Ar} \diagdown \overset{\displaystyle A}{\underset{\displaystyle O-(CH_2)_m-N \diagup R_1 \diagdown R_2}{\bigcirc}}(R)_n \quad (I)$$

in which:

R represents a hydrogen or halogen atom or a methyl, hydroxyl, $C_1-C_4$ alkoxy or benzyloxy group;

n takes the value 1 or 2 when R is different from H;

m takes the value 2 or 3;

A represents a chain having any of the following structures:

$$\overset{1}{C}O-\overset{2}{C}H_2-\overset{3}{C}H_2, \quad \overset{1}{C}H-\overset{2}{C}H_2-\overset{3}{C}H_2, \quad \overset{1}{C}H-\overset{2}{\underset{\underset{CH_3}{|}}{C}}-\overset{3}{C}H_2,$$
$$\phantom{xxxxxxxxxx} | \phantom{xxxxxxx} |$$
$$\phantom{xxxxxxxxxx} OH \phantom{xxxxx} OH$$

$$\overset{1}{C}O-\overset{2}{\underset{\underset{CH_3}{|}}{\overset{\overset{CH_3}{|}}{C}}}-\overset{3}{C}H_2, \quad \overset{1}{C}H_2-\overset{2}{C}H_2-\overset{3}{C}H_2$$

the aromatic group Ar being bonded to position 1 of this chain, the pair ($R_1$, $R_2$) takes the value (H, $C_1-C_4$ alkyl), (H, $C_5-C_6$ cycloalkyl) or (H, cycloalkylalkyl comprising 4 to 8 carbon atoms), except in the case where $$A = CO\diagdown\underset{CH_3}{\overset{CH_3}{\diagup}}C-CH_2 \quad \text{or} \quad CH-\underset{\underset{CH_3}{|}}{\overset{\overset{CH_3}{|}}{C}}-CH_2,$$
$$\phantom{xxxxxxxxxxxxx} |$$
$$\phantom{xxxxxxxxxxxxx} OH$$

or else the value ($C_1-C_4$ alkyl, $C_1-C_4$ alkyl), $R_1$ and $R_2$ being also able to form jointly with the nitrogen atom with which they are bonded, a radical chosen from the following: pyrrolidino, piperidino, hexamethyleneimino, morpholino; and Ar represents:

either a benzenic group of structure:

$$\underset{(R_4)_q}{\overset{(R_3)_p}{\bigcirc}}$$

in which $R_3$ represents a halogen atom or a nitro or methyl group, $R_4$ = alkoxy with 1 to 4 carbon atoms, p=0, 1 or 2, q=0, 1, 2, 3 or 4, p+q≦4, with the restrictions that when $$A = CO-CH_2-CH_2 \quad \text{or} \quad \underset{\underset{OH}{|}}{CH}-CH_2-CH_2$$

p and q cannot take simultaneously the value 0, or a naphthalenic or benzodioxannic group respectively of structure:

$$\underset{R_4}{\overset{R_4}{\bigcirc\bigcirc}} \quad \underset{R_4}{\overset{R_4}{[\bigcirc]}}$$

where $R_4$ has the same meanings as above.

2. The method of claim 1, wherein said troubles of the cerebrovascular system comprise cerebral hemorrhages, cerebral infarction and migraine.

3. The method according to claim 1, wherein A represents the chain of structure $$\overset{1}{C}O-\overset{2}{C}H_2-\overset{3}{C}H_2.$$

4. The method according to claim 3, wherein

[Ar(/\O), (R)n, m, NR₁R₂]

takes the value ( [3,5-dimethoxy-2-methylphenol-piperidine] , 4-OH, 2, N⟨piperidine⟩ ), ( [5-chloro-4-methoxy-2-methyl-3-methoxyphenol-piperidine] , 4-OH, 2, N⟨piperidine⟩ ), ( [5-chlorophenol-piperidine] , 4-OH, 2, N⟨piperidine⟩ ) ou ( [3-methoxy-5-methoxyphenol-piperidine] , 4-OH, 2, N⟨piperidine⟩ ).

5. The method according to claim 1, wherein A represents the chain of structure:

$$CO-\underset{\underset{CH_3}{|}}{\overset{\overset{CH_3}{|}}{C}}-CH_2$$

6. The method according to claim 5, wherein

[Ar(/\O), (R)n, m, NR₁R₂]

takes any one of the following values:

( [phenol] , 4-OCH₂φ, 2, N⟨piperidine⟩ ), ( [phenol] , 4-OH, 2, N⟨piperidine⟩ ), ( [3,5-dimethoxy-chlorophenol] , 4-OH, 2, N⟨piperidine⟩ ).

7. The method according to claim 1, wherein A represents the chain of structure

CH₂—CH₂—CH₂

8. The method according to claim 7, wherein

[Ar(/\O), (R)n, m, NR₁R₂]

takes any one of the following values:

( [3,5-dimethoxyphenol] , 4-OH, 2, N⟨piperidine⟩ ), ( [5-chloro-3-methoxyphenol] , 4-OH, 2, N⟨piperidine⟩ ).

9. The method according to claim 1, wherein A represents the chain $$\underset{\underset{}{}}{\overset{\overset{OH}{|}}{CH}}-CH_2-CH_2.$$

10. The method according to claim 9, wherein takes any one of the following values:

( [2-methoxy-4-methoxyphenol] , H, 2, N⟨piperidine⟩ );

( [3,5-dimethoxyphenol] , 4-F, 2, N⟨piperidine⟩ )

( [3-methoxy-5-methoxyphenol] , 4-Cl, 2, N⟨piperidine⟩ );

(2,6-diOCH₃-4-CH₃-phenoxy, 2, piperidinyl);

(2,6-diOCH₃-4-OCH₃-phenoxy, 2, piperidinyl);

(2-OCH₃-6-OCH₃, 2-OH, 2, piperidinyl);

(2-OCH₃-6-OCH₃, 3-OH, 2, piperidinyl);

(2,6-diOCH₃-phenoxy, 4-OH, 2, piperidinyl);

(2,6-diOCH₃-phenoxy, 4-OH, 3, piperidinyl);

(2,6-diOCH₃-phenoxy, 4-OH, 2, N(Et)₂);

(2,5-diOCH₃-phenoxy, 4-OH, 2, piperidinyl);

(2,3,5-triOCH₃-phenoxy, 4-OH, 2, piperidinyl);

(2,3,4-triOCH₃-phenoxy, 4-OH, 2, piperidinyl);

(2-OCH₃-phenoxy, 4-OH, 2, piperidinyl);

(2,6-diOCH₃-phenoxy, 4-OH, 2, morpholinyl);

(2,6-diOCH₃-phenoxy, 4-OH, 2, N(CH₃)₂);

(2,3,5-triOCH₃-phenoxy, 4-OH, 2, N(Et)₂);

(2-OCH₃-phenoxy, 4-OH, 2, N(Et)₂);

(2,3,5-triOCH₃-phenoxy, 4-OCH₂φ, 2, piperidinyl);

(2,6-diOCH₃-phenoxy, 3,4-diOCH₂φ, 2, piperidinyl);

(2,6-diOCH₃-phenoxy, 3,4-diOH, 2, piperidinyl);

-continued (3,5-dimethoxy-2-methylphenol), 4-OH, 2, 2,6-dimethylpiperidinyl;

(3,5-dimethoxy-2-methylphenol), 4-OH, 2, piperidinyl);

(2,5-diethoxy-phenol), 4-OH, 2, N(Et)₂);

(2,5-diethoxy-phenol), 4-OCH₂φ, 2, N(Et)₂);

(3,6-dimethoxy-2-methylphenol), 4-OH, 2, NH-cyclopentyl);

(methylenedioxy-methoxy-methylphenol), 4-OH, 2, piperidinyl);

(trimethoxy-methylphenol), 4-OH, 2, piperidinyl);

(1,4-dimethoxy-naphthol), 4-OH, 2, piperidinyl);

(5-chloro-3-methoxy-2-methylphenol), 4-OH, 2, piperidinyl);

-continued (5-chloro-3-methoxy-2-methylphenol with CH₃), 4-OH, 2, N(Et)₂), (5-chloro-3-methoxy with CH₃), 4-OH, 2, 2,6-dimethylpiperidinyl), (5-fluoro-3-methoxy with OCH₃), 4-OH, 2, piperidinyl), (chloro-dimethoxy), 4-OH, 2, piperidinyl), (nitro-dimethoxy), 4-OH, 2, piperidinyl), (3,6-dichloro), 4-OH, 2, piperidinyl), (5-chloro), 4-OH, 2, piperidinyl), (5-chloro-3,6-dimethoxy), H, 2, piperidinyl), (5-chloro-3,6-dimethoxy), 4-OCH₂φ, 2, piperidinyl), 11. The method according to claim 1, wherein A represents the chain of structure:

$$\begin{array}{ccc} OH & CH_3 \\ | & | \\ CH-C-CH_2 \\ | \\ CH_3 \end{array}$$

12. The method according to claim 11, wherein $$[Ar\diagdown_O^{\diagup}, (R)n, m, NR_1R_2]$$

takes the value:

(⏣ , 4-OH, 2, N⏣) or (⏣[CH₃O, CH₃O, Cl], 4-OH, 2, N⏣).

* * * * *